US00PP15316P2

(12) United States Plant Patent
Hooijman

(10) Patent No.: US PP15,316 P2
(45) Date of Patent: Nov. 16, 2004

(54) *ASTER* PLANT NAMED 'ESMART'

(50) Latin Name: *Aster hybrida*
Varietal Denomination: Esmart

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/770,219

(22) Filed: Feb. 2, 2004

(51) Int. Cl.[7] ..... A01H 5/00
(52) U.S. Cl. ..... Plt./355
(58) Field of Search ..... Plt./355

*Primary Examiner*—Kent Bell
(74) *Attorney, Agent, or Firm*—C. A. Whealy

(57) ABSTRACT

A new and distinct cultivar of cut flower *Aster* plant named 'Esmart', characterized by its strong erect flowering stems; symmetrical branching habit; dark green-colored foliage; uniform and freely flowering habit; decorative-type inflorescences with violet-colored ray florets; and good postproduction longevity.

1 Drawing Sheet

Botanical classification/cultivar designation: *Aster hybrida* cultivar Esmart.

BACKGROUND OF THE INVENTION

The present Invention relates to a new and distinct cultivar of cut flower *Aster* plant, botanically known as *Aster hybrida* and hereinafter referred to by the name 'Esmart'.

The new *Aster* is a product of a planned breeding program conducted by the Inventor in El Quinche, Pichincha, Ecuador. The objective of the breeding program is to create new cut flower *Aster* cultivars with durable leaves, strong stems, desirable floret colors, and good postproduction longevity.

The new *Aster* originated from a cross-pollination made by the Inventor in El Quinche, Pichincha, Ecuador in August, 1999, of a proprietary *Aster* selection identified as breeding line 13, not patented, as the female, or seed, parent with an unknown *Aster* selection, not patented, as the male, or pollen, parent. The new *Aster* was discovered and selected by the Inventor as a single flowering plant within the progeny of the stated cross-pollination grown in a controlled environment in El Quinche, Pichincha, Ecuador. The selection of this plant was based on its durable foliage, strong stems and desirable inflorescence form and ray floret color.

Asexual reproduction of the new *Aster* by vegetative tip cuttings was first conducted in El Quinche, Pichincha, Ecuador in August, 2000. Asexual reproduction by cuttings has shown that the unique features of this new *Aster* are stable and reproduced true to type in successive generations.

SUMMARY OF THE INVENTION

The cultivar Esmart has not been observed under all possible environmental conditions. The phenotype may vary somewhat with variations in environment such as temperature, daylength and/or light level, without, however, any variance in genotype.

The following traits have been repeatedly observed and are determined to be the unique characteristics of 'Esmart'. These characteristics in combination distinguish 'Esmart' as a new and distinct cut flower *Aster:*

1. Strong erect flowering stems.
2. Symmetrical branching habit.

3. Dark green-colored foliage.
4. Uniform and freely flowering habit.
5. Decorative-type inflorescences with violet-colored ray florets.
6. Good postproduction longevity.

Plants of the new *Aster* are taller than plants of the female parent selection. In addition, plants of the new *Aster* differ from plants of the female parent selection in ray floret coloration.

Plants of the new *Aster* can be compared to plants of the cultivar Cirina, not patented. In side-by-side comparisons conducted in El Quinche, Pichincha, Ecuador plants of the new *Aster* differed from plants of the cultivar Cirina in the following characteristics:

1. Plants of the new *Aster* were more vigorous than plants of the cultivar Cirina.
2. Plants of the new *Aster* had stronger flowering stems than plants of the cultivar Cirina.
3. Plants of the new *Aster* had larger and darker-green colored leaves than plants of the cultivar Cirina.
4. Plants of the new *Aster* had larger inflorescences with more ray and disc florets per inflorescence than plants of the cultivar Cirina.
5. Inflorescences of plants of the new *Aster* had more phyllaries than inflorescences of plants of the cultivar Cirina.
6. Plants of the new *Aster* had longer peduncles than plants of the cultivar Cirina.
7. Plants of the new *Aster* and the cultivar Cirina differed in ray floret coloration as plants of the cultivar Cirina had purple violet-colored ray florets.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster.*

The photograph at the top of the sheet comprises a side perspective view of a typical flowering plant of 'Esmart'.

The photograph at the bottom of the sheet comprises a close-up view of a typical inflorescence of 'Esmart'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the summer in El Quinche, Pichincha, Ecuador, in an outdoor nursery and under conditions which approximate those generally used in commercial cut flower *Aster* production. During the production of these plants, day temperatures ranged from 12 to 30° C. and night temperatures ranged from 5 to 12° C. Plants were about four to six months from planting rooted young plants when the photographs and the botanical description were taken.

Botanical classification: *Aster hybrida* cultivar Esmart.

Parentage:

*Female, or seed, parent.*—Proprietary *Aster hybrida* selection identified as breeding line 13, not patented.

*Male, or pollen, parent.*—Unknown *Aster hybrida* selection, not patented.

Propagation:

*Type.*—Terminal vegetative cuttings.

*Time to initiate roots.*—About 12 to 16 days at 17 to 25° C.

*Time to produce a rooted young plant.*—About 21 to 25 days at 17 to 25° C.

*Root description.*—Fine, fibrous; moderately dense; 162D to 161D in color.

*Rooting habit.*—Freely branching.

Plant description:

*Appearance.*—Herbaceous decorative-type cut flower *Aster*. Flowering stems upright and strong. Vigorous. Symmetrical branching habit.

*Plant height.*—About 126 cm.

*Plant width.*—About 20 cm.

*Lateral branches.*—Quantity per plant: About 21. Length: About 124 cm. Diameter: About 7.5 mm. Internode length: About 2.3 cm. Strength: Strong. Texture: Glabrescent; waxy. Color: 144B.

*Foliage description.*—Arrangement: Alternate, simple; sessile. Quantity per lateral branch: About 150. Length: About 13.5 cm. Width: About 2.4 cm. Shape: Narrowly ovate. Apex: Acute. Base: Cordate. Margin: Dentate. Texture, upper and lower surfaces: Glabrous, smooth; waxy. Color: Developing foliage, upper surface: 137A. Developing foliage, lower surface: 137B. Fully expanded foliage, upper surface: 147A; venation, 147B. Fully expanded foliage, lower surface: 137C; venation, 147B.

Inflorescence description:

*Appearance.*—Decorative-type inflorescence form with narrowly elliptic-shaped ray florets. Inflorescences terminal or axillary. Disc and ray florets develop acropetally on a capitulum. Inflorescences not fragrant. Inflorescences persistent. Inflorescences face mostly upright. Uniform and freely flowering habit.

*Flowering response.*—Plants flower year-round in Ecuador.

*Postproduction longevity.*—Inflorescences maintain good color and substance for about two weeks as a cut flower and about 25 days on the plant.

*Quantity of inflorescences.*—About eleven inflorescences develop per lateral branch.

*Inflorescence bud.*—Height: About 7.9 mm. Diameter: About 6.4 mm. Shape: Nearly globose. Color: 132A to 132B.

*Inflorescence size.*—Diameter: About 3.7 cm. Depth (height): About 1.3 cm. Diameter of disc: About 1 cm. Receptacle height: About 6.5 mm. Receptacle diameter: About 1 cm.

*Ray florets.*—Number of ray florets per inflorescence/arrangement: About 73 arranged in two or three whorls. Length: About 1.6 cm. Width: About 3 mm. Shape: Narrowly elliptic. Apex: Obtuse with emarginations. Base: Attenuate. Margin: Entire. Texture, upper and lower surfaces: Smooth, glabrous; papery. Orientation: Initially upright, then mostly horizontal. Aspect: Mostly straight. Color: When opening, upper surface: N87A. When opening, lower surface: N86D. Fully opened, upper surface: N87A; becoming closer to N87C with development. Fully opened, lower surface: 90C.

*Disc florets.*—Arrangement: Massed at center of receptacle. Number of disc florets per inflorescence: About 78. Length: About 9 mm. Diameter, apex: About 1.9 mm. Diameter, base: About 1.7 mm. Shape: Tubular, salverform, elongated. Apex: Acute. Color, immature: 151B. Color, mature: 145C.

*Phyllaries.*—Quantity per inflorescence: About 57. Length: About 9 mm. Width: About 1.7 mm. Shape: Narrowly deltoid. Apex: Acute. Base: Truncate. Texture, upper and lower surfaces: Smooth, glabrous. Color, upper surface: 137A. Color, lower surface: 137C.

*Peduncles.*—Length, terminal peduncle: About 2.4 cm. Length, fourth peduncle: About 5.6 cm. Length, seventh peduncle: About 7 cm. Diameter: About 1.3 mm. Aspect: Erect to about 21° from vertical. Strength: Strong. Texture: Pubescent. Color: 137C.

*Reproductive organs.*—Androecium: Present on disc florets only. Quantity per disc floret: One. Anther shape: Linear. Anther length: About 1 mm. Anther color: 7B. Pollen amount: Scarce. Pollen color: 7B. Gynoecium: Present on both ray and disc florets. Quantity per floret: One. Pistil length: About 7.4 mm. Stigma shape: Bilobed. Stigma color: 145C. Style length: About 6.2 mm. Style color: 145C. Ovary color: 145D.

*Seed.*—Length: With pappus, about 5 mm; without pappus, about 3 mm. Diameter: About 1 mm. Color: 145D; dried, 199A.

Disease/pest resistance: Resistance to pathogens and pests common to *Asters* has not been observed on plants grown under commercial greenhouse conditions.

Temperature tolerance: Plants of the new *Aster* have been observed to tolerate temperatures from 5 to over 30° C.

It is claimed:

1. A new and distinct cultivar of cut flower *Aster* plant named 'Esmart', as illustrated and described.

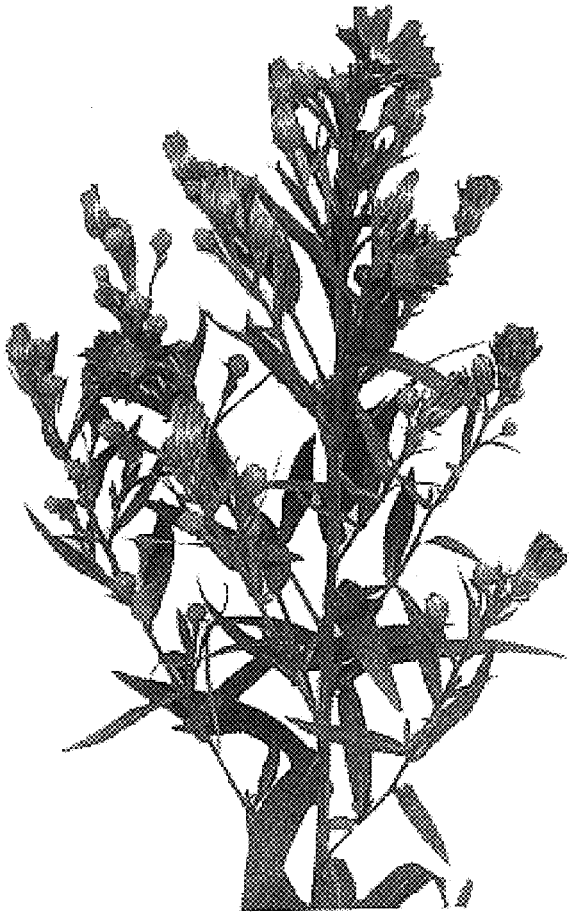
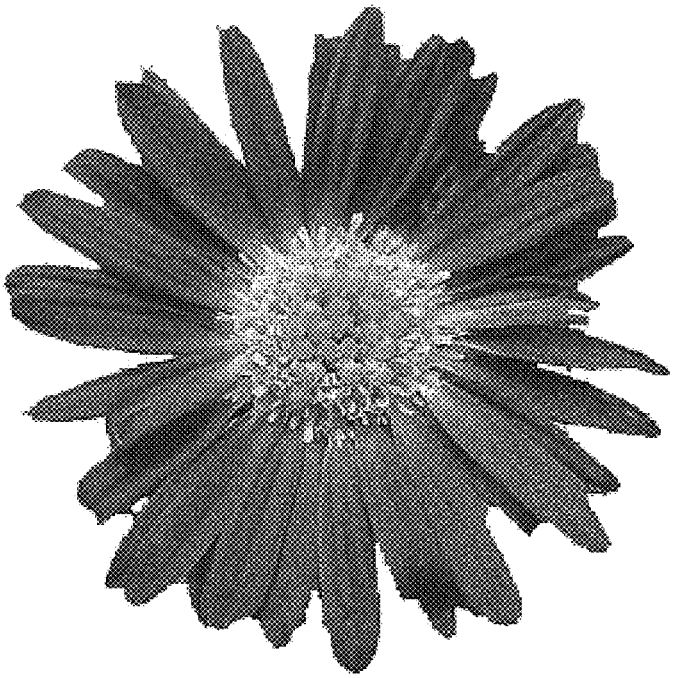

* * * * *